United States Patent [19]
Trigg et al.

[11] Patent Number: 5,545,408
[45] Date of Patent: Aug. 13, 1996

[54] BIOCOMPATIBLE IMPLANT FOR THE TIMING OF OVULATION IN MARES

[75] Inventors: Timothy E. Trigg, Warrawee, Australia; Edward L. Souires, Fort Collins, Colo.; Wolfgang Jochle, Denville, N.J.

[73] Assignee: Peptide Technology Limited, Australia

[21] Appl. No.: 211,794

[22] PCT Filed: Oct. 19, 1992

[86] PCT No.: PCT/AU92/00557

§ 371 Date: Jun. 15, 1994

§ 102(e) Date: Jun. 15, 1994

[87] PCT Pub. No.: WO93/07833

PCT Pub. Date: Apr. 29, 1993

[30] Foreign Application Priority Data

Oct. 21, 1991 [AU] Australia ................... PK9037

[51] Int. Cl.$^6$ ............. A61D 19/00; A61D 7/00
[52] U.S. Cl. ........... 424/422; 424/423; 424/425; 424/426; 514/8; 514/12; 514/13; 514/14; 514/15; 514/21; 119/174
[58] Field of Search .............. 119/174; 514/12, 514/8, 13, 14, 15, 21; 424/422, 423, 425, 426

[56] References Cited

U.S. PATENT DOCUMENTS 4,010,125  3/1977  Schally et al. ................. 260/8
4,589,402  5/1986  Hodgen et al. ................. 128/1

FOREIGN PATENT DOCUMENTS 586252  11/1986  Australia .
2166951  5/1986  United Kingdom .

OTHER PUBLICATIONS

Chemical Abstracts 112:152152, "Use of Gonadotropin-Releasing Hormone for Hastening Ovulation in Transitional Mares", Harrison et al.

Derwent Abstracts Accession No. 87–329107/47, Class P32, EP, A, 246910 (Gene Link Aust. Ltd.) 25 Nov. 1987 (25.11.87). p. 6 lines 2–11.

Derwent Soviet Inventions Illustrated, Section 1, Chemical, vol. X, No. 14, Issued 12 May 1976, Pharmaceuticals, p. 1, SU 475136 (Livestock Farm Res) 19 Sep. 1975 (19.9.75).

Derwent Soviet Inventions Illustrated, Section 1, Chemical, vol. U, No. 37, Issued 18 Oct. 1973, Pharmaceuticals, p. 4, SU 367866 (Livestock Breeding Res. Inst.) 30 Mar. 1973 (30.3.73).

Primary Examiner—Frederick Krass
Attorney, Agent, or Firm—Banner & Allegretti, Ltd.

[57] ABSTRACT

The disclosed invention relates to a method for controlling the timing of the ovulation of mares using an LHRH agonist, and to a biocompatible implant for use in such a method.

15 Claims, 6 Drawing Sheets

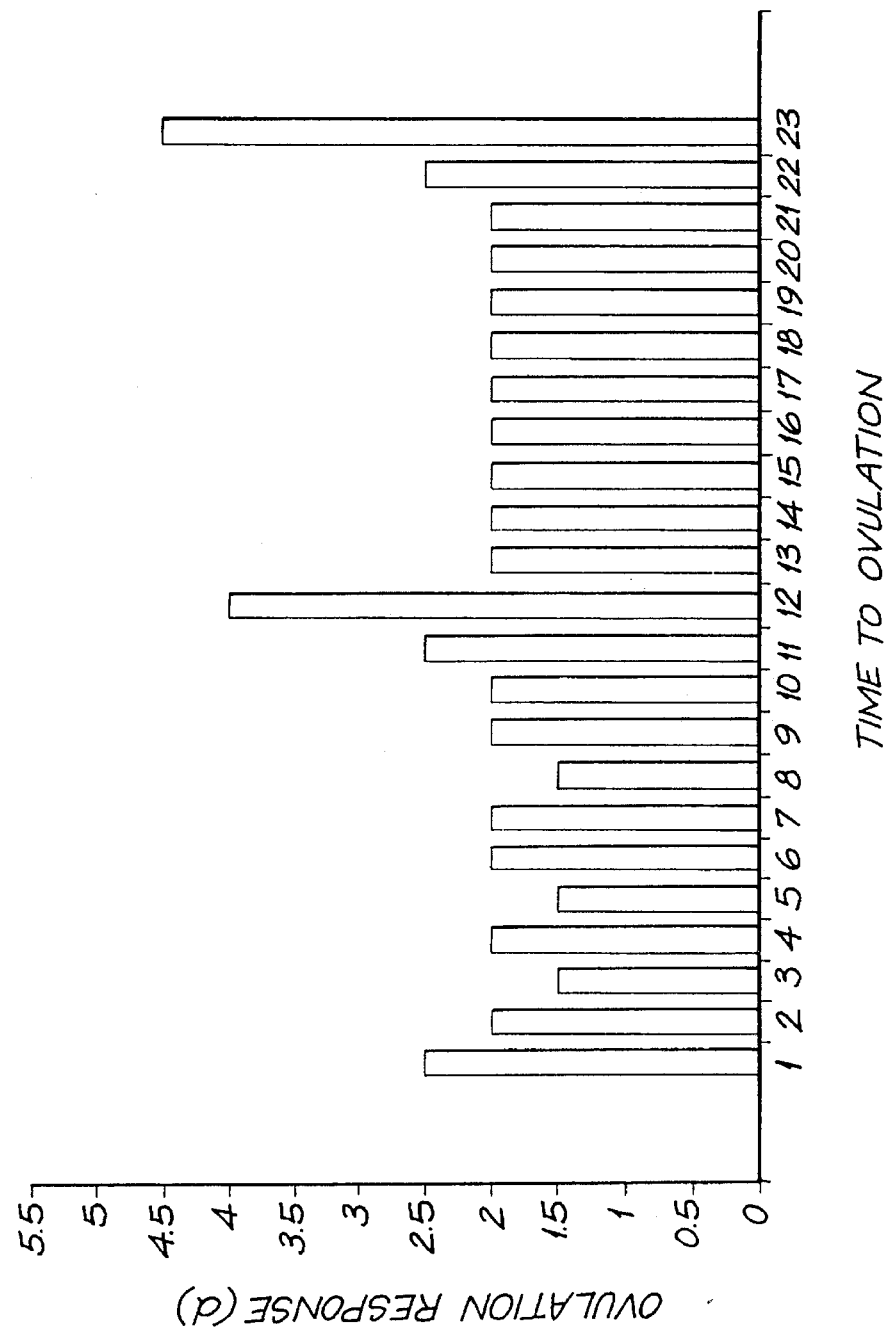

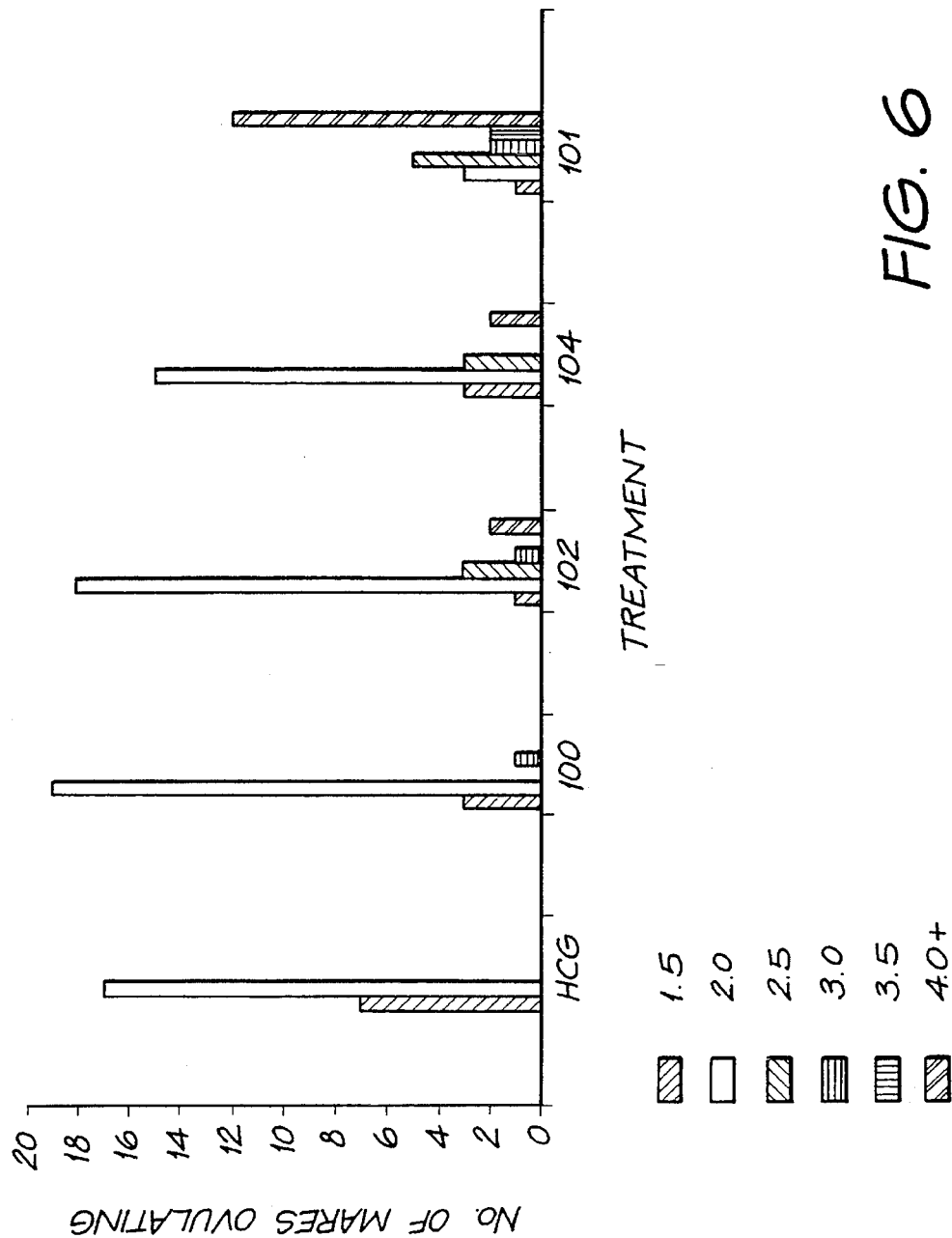

BIOCOMPATIBLE IMPLANT FOR THE TIMING OF OVULATION IN MARES

FIELD OF THE INVENTION

The present invention relates to a method for controlling the timing of the ovulation of mares and to a biocompatible implant for use in such a method.

BACKGROUND ART

The equine industry worldwide is continually improving breeding management. This improvement is driven by many factors; of significance are (i) the need to conserve "stallion power" and (ii) the veterinarians requirement to improve their efficiency by having mares ovulate with more predictability.

In order to achieve the above, the ability to predict, within predetermined time constraints when a mare will ovulate, is critical. The use of injection of human chorionic gonodotrophin (HCG) to stimulate ovulation in mares between 36–48 hours after application is widespread. However, despite success with this hormone, it has a number of serious drawbacks.

They include:

(i) it is not registered for this use in many countries (USA, and areas of Europe). Veterinarians using hCG in countries where it is unregistered are liable for any claims against failure of the product.

(ii) continued used in the same mare can cause refractiveness—anaphylaxis is a possibility.

(iii) hCG is derived from human urine either from pregnant or post menopausal women. Collection, isolation and purification are unpleasant, and the possibility of transmission of disease, particularly those of viral origin, is a risk.

(iv) supplies of hCG cannot be guaranteed.

As an alternative to hCG, Leutinising Hormone Releasing Hormone (LHRH) has been injected into mares to stimulate ovulation. LHRH is also known as Gonodotrophin releasing hormone (GnRH). The LHRH stimulates the mare to produce its own gonodotrophin which, in turn, stimulates ovulation. An agonist of LHRH (Buserelin) has also been injected into mares and it has been reported that ovulation may be induced by such injections. Injected hormones must be typically administered a number of times to be successful and they are required in relatively large doses.

DISCLOSURE OF THE INVENTION

The present invention is directed to an alternative method and composition for controlling the timing of ovulation in mares.

In a first aspect the present invention consists in a method for the controlled induction of ovulation in mares comprising implanting into a mare which already has an ovarian follicle approaching maturation a solid biocompatible implant comprising a solid carrier and an effective amount of an agonist of LHRH so as to increase the level of LHRH agonist in the mare above that prevailing immediately before that implantation.

In a second aspect the present invention consists in a solid biocompatible implant for controlling the induction of ovulation in mares which already have an ovarian follicle approaching maturation, the implant comprises a biologically absorbable solid and from 1.0 to 5.0 mg of an agonist of LHRH.

Deslorelin is a peptide and a super agonist for LHRH. It is the most preferred LHRH agonist for use in the present invention. The formula for Deslorelin is:

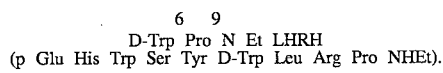

As used herein the term "an ovarian follicle approaching maturation" is taken to mean an ovarian follicle which has developed to a size of at least about 30 mm in diameter.

Deslorelin has the particular advantage that its efficacy in the induction of ovulation in mares is sufficiently high that the biocompatible implant may be made small enough to be very acceptable in practice. There are however a number of other LHRH agonists which could be used in carrying out the present invention. These include the following compounds as discussed in Dutton, A. S., "Luteinizing Hormone—Releasing Hormone (LHRH) Agonists", Drugs of the Future, Vol 13, No. 1, 1988:

| Agonist Structure | Name (Company) |
|---|---|
| [D-Ser(But⁶.des-Gly—NH₂¹⁰]—LHRK(1–9)NHEt | Buserelin (Hoechst) |
| [D-Trp⁶]—LHRH | Tryptorelin (Debiopharm) (Decapeptyn) |
| [des-Gly—NH₂¹⁰]—LHRH(1–9)NHEt | Fertirelin (Takeda) |
| [D-His(Bz)⁶, des-Gly—NH₂¹⁰]—LHRH(1–9)NHEt | Histrelin (Ortho) |
| [D-Leu⁶, des-Gly—NH₂¹⁰]—LHRH(1–9)NHEt | Leuprolide (Abbott) |
| [D-Trp⁶, MeLeu⁷, des-Gly—NH₂¹⁰]—LHRH(1–9)NHEt | Lutrelin (Wyeth) |
| [D-Nal(2)⁶]—LHRH | Nafarelin (Syntex) |
| [D-Ser(Buᵗ)⁶, Azgly¹⁰)—LHRH | Zoladex (Registered Trade Mark) ICI |

In addition the following LHRH agonists may be used in carrying out the invention:

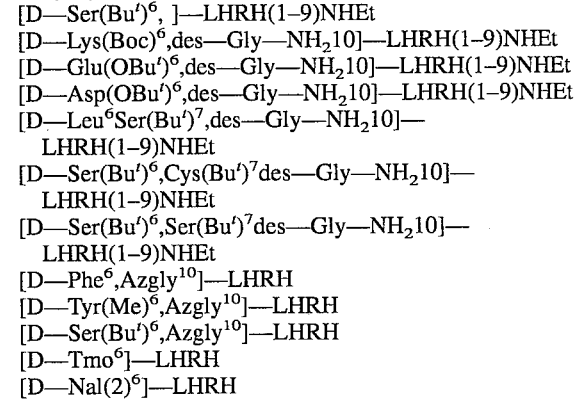

[D—Ptf⁶]—LHRH
[D—Tmp⁶]—LHRH
[D—Bpal⁶]—LHRH
[D—Nal(2)⁶MeLeu⁷]—LHRH
[D—Nal(2)⁶MeLeu⁷,des—Gly—NH$_2$¹⁰]—LHRH—1–9NHEt
[D—hArg(Et$_2$)⁶]—LHRH
[D—hArg(Me,Bu)⁶]—LHRH
[D—hArg(Et$_2$)⁶,des—Gly—NH$_2$¹⁰]—LHRH—1–9NHEt
[D—hArg(Me,Bu)⁶,des—Gly—NH$_2$¹⁰]—LHRH—1–9NHEt The solid carrier for the LHRH or LHRH agonist should be a material into which the Deslorelin can be mixed or absorbed, onto which it may be adsorbed, or onto which it may be coated. It is a particularly preferred feature of the invention that the carrier is a biologically adsorbable inorganic salt such as calcium phosphate dihydrate, calcium phosphate, sodium sulphate or calcium carbonate. This allows the biocompatible implant to be made cheaply by a simple tableting technique. To assist in forming the implant and to provide an improved active release profile it is preferred that the implant contains a small proportion of an organic tablet release compound or lubricating agent such as a fatty acid or a hydrogenated vegetable oil. The tablet release compound preferably comprises from 4 to 10% by weight of the implant and more preferably about 8%. It has been found that the release characteristics of the LHRH agonist from such an inorganic salt mixed with such lubricating agent is such that ovulation can be induced in a tightly controlled manner, i.e., that a high proportion of the mares will ovulate at a given time after the administration of the implant.

The implant is desirably as small as possible. Preferably the implant is substantially cylindrical having a diameter of from 0.5 to 5 mm and a length of from 1 to 6 mm. Obviously other sizes and shapes of biocompatible implants may be used however the selection of preferred embodiments of the present invention allows the size of the implant to be sufficiently small to be of practical utility. The implant is preferably small enough to be able to be implanted into a mare through a tubular needle. The needle is inserted into the mare, such as in the neck region, and the implant pushed down the needle with an obturator as the needle is withdrawn. This leaves the implant embedded subcutaneously in the animal. The LHRH agonist is released from the implant in a controlled manner and the carrier is slowly dissolved.

The LHRH agonist should preferably be present in the implant in an amount of from 1.0 to 5.0 mg, more preferably 1.5 to 3.0 mg and most preferably 2.0 to 2.4 mg for a thoroughbred mare of average size.

BRIEF DESCRIPTION OF THE DRAWINGS

Hereinafter given by way of example only are preferred embodiments of the present invention described with reference to the accompanying figures in which:

FIGS. 3 to 6 show ovulation response to treatments as described in Example 3.

BEST METHOD FOR CARRYING OUT THE INVENTION

In all examples, unless indicated otherwise, short term implants of the LHRH agonist Deslorelin were prepared by mixing the Deslorelin with finely ground calcium carbonate and 5% of a hydrogenated vegetable oil tableting aid sold under the trade mark "LUBRITAB" (Edward Mendell Co. Inc, New York, U.S.A). The mixture is then tableted to the desired shape in a conventional manner. The implants were substantially cylindrical having a diameter of 2.3 mm and a length of 3.4 mm. All treatments with hCG were by injection.

EXAMPLE 1

Figure 1:
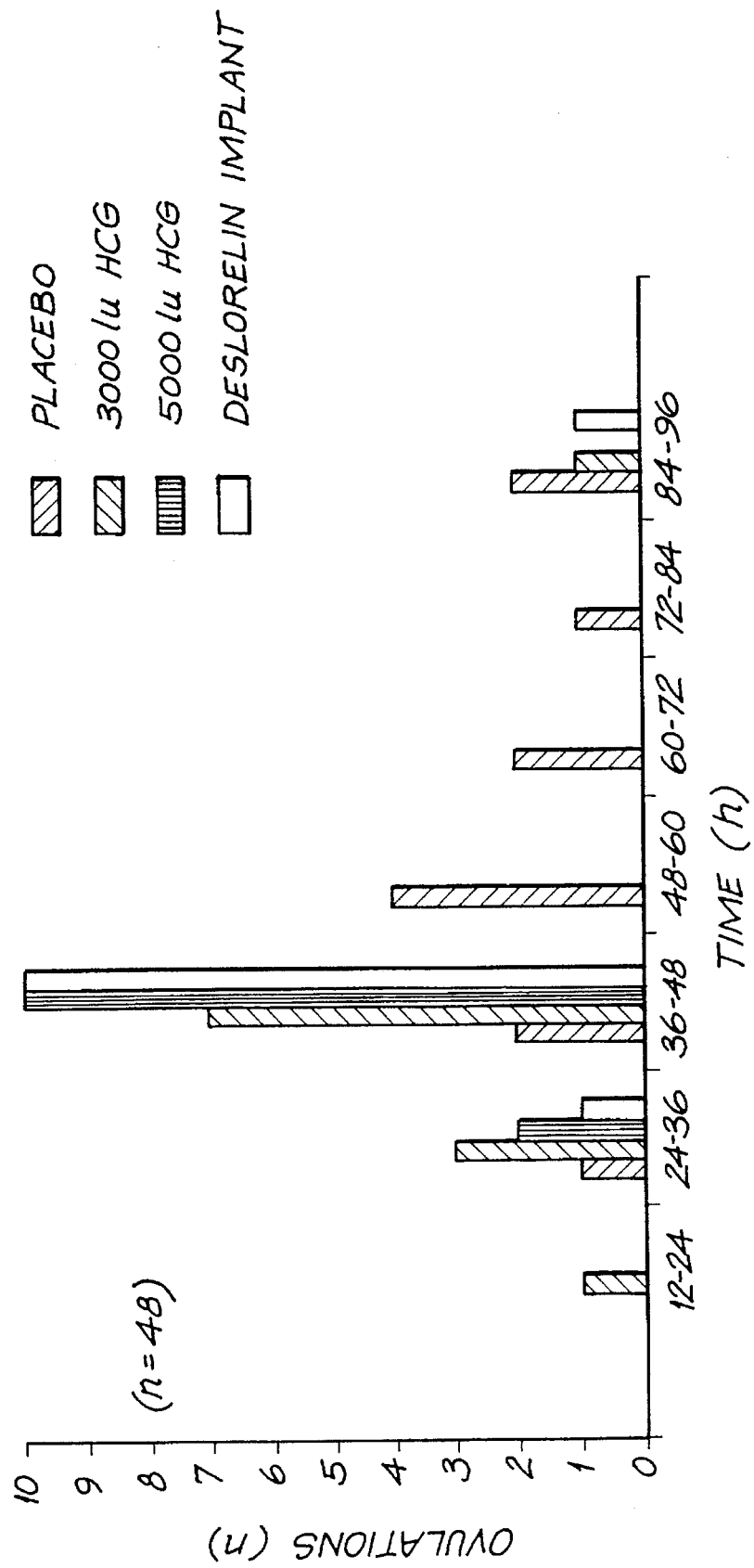
FIG. 1 shows time to ovulation for mares treated as described in Example 1.

Groups of twelve Hannovarian mares were each given a placebo implant, injected with either 3,000 iuhCG or with 5,000 iuhCG or given an implant containing 1.5 mg of Deslorelin. In this example treatment was given when the mares showed follicles of 40 mm diameter as the horses were Hannovarian. The results of this example are shown in FIG. 1. It can be seen that the 1.5 mg Deslorelin implant performed as well as 3,000 iuhCG and possibly as well as 5,000 iuhCG.

EXAMPLE 2

Figure 2:
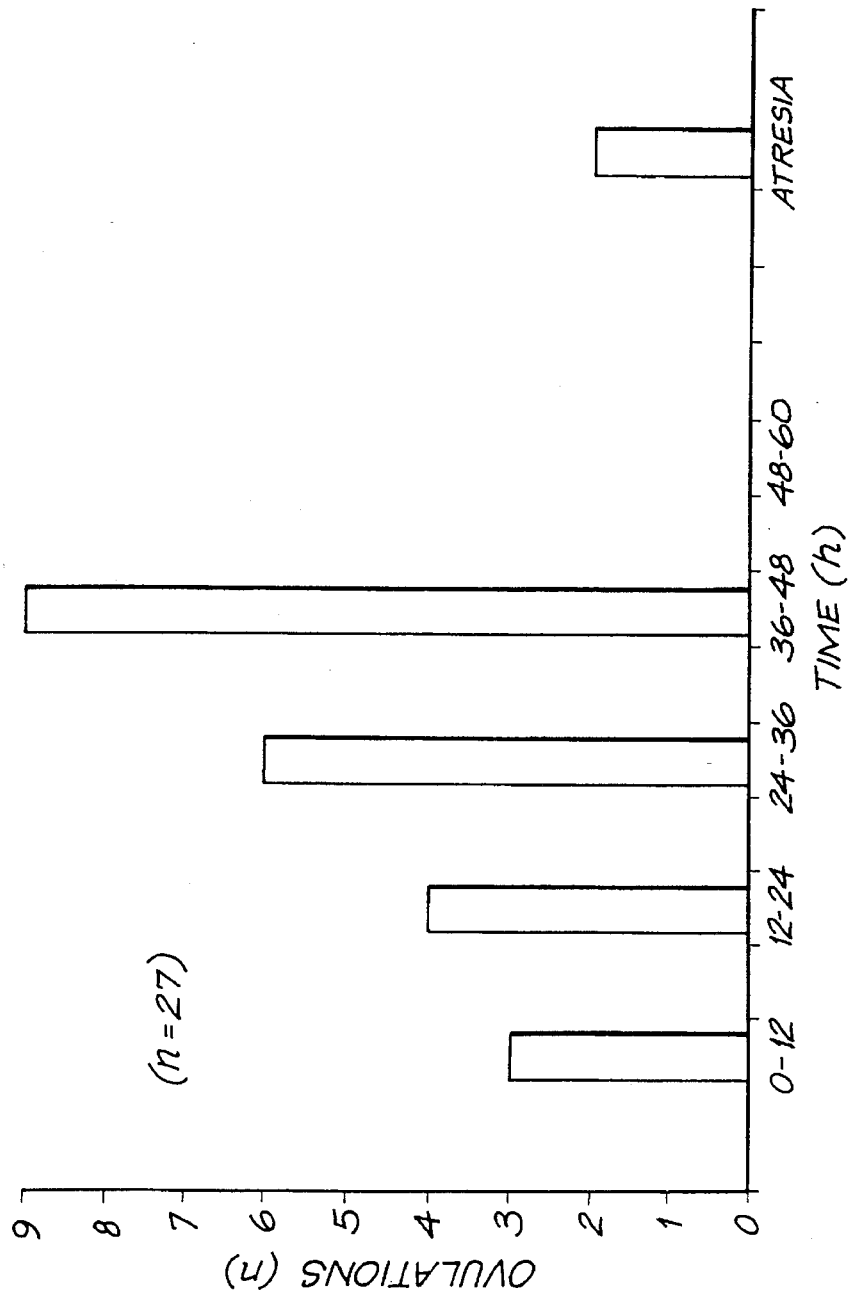
FIG. 2 shows time to ovulation after treatment with a short term implant containing 2.25 mg of LHRH as described in Example 2.
Figure 3:
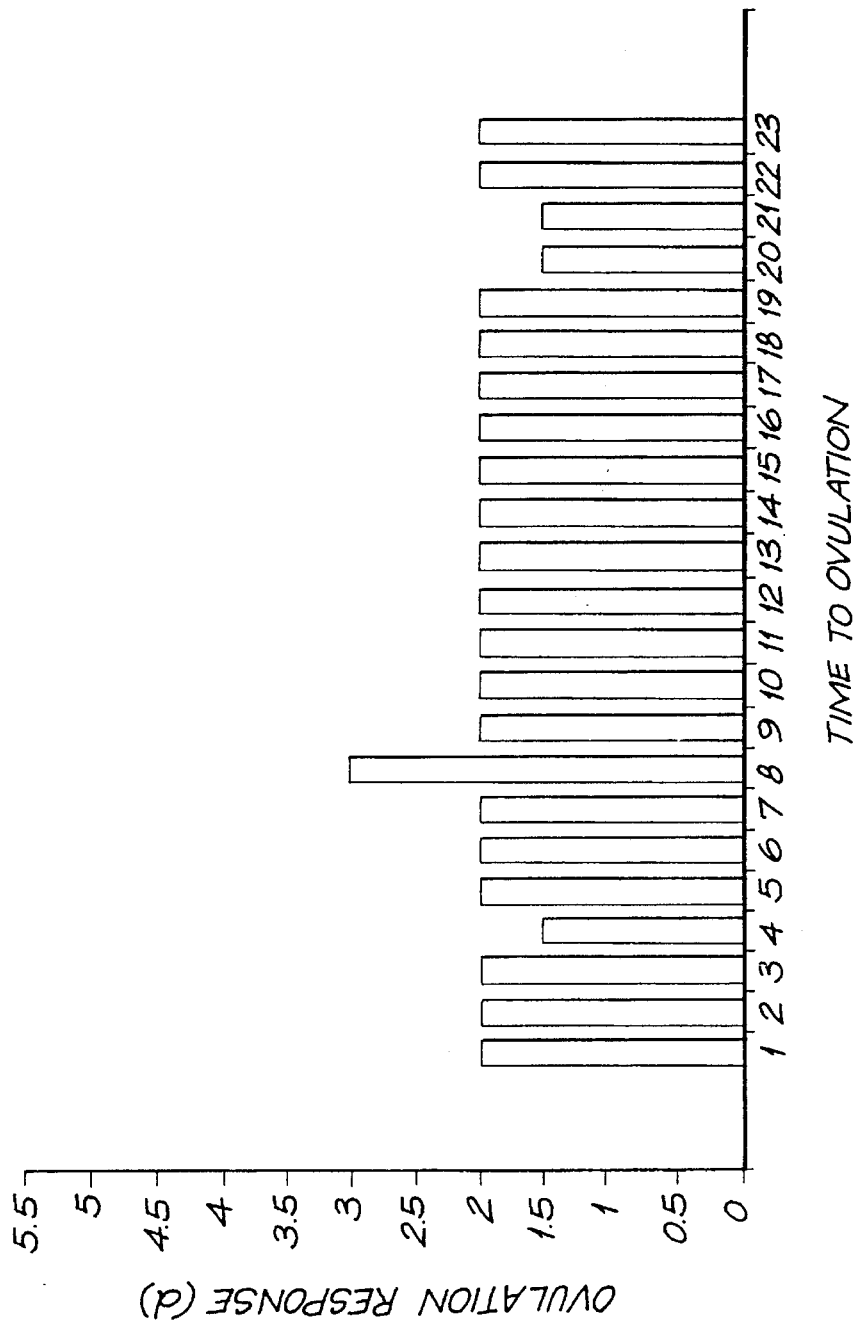
Figure 4:
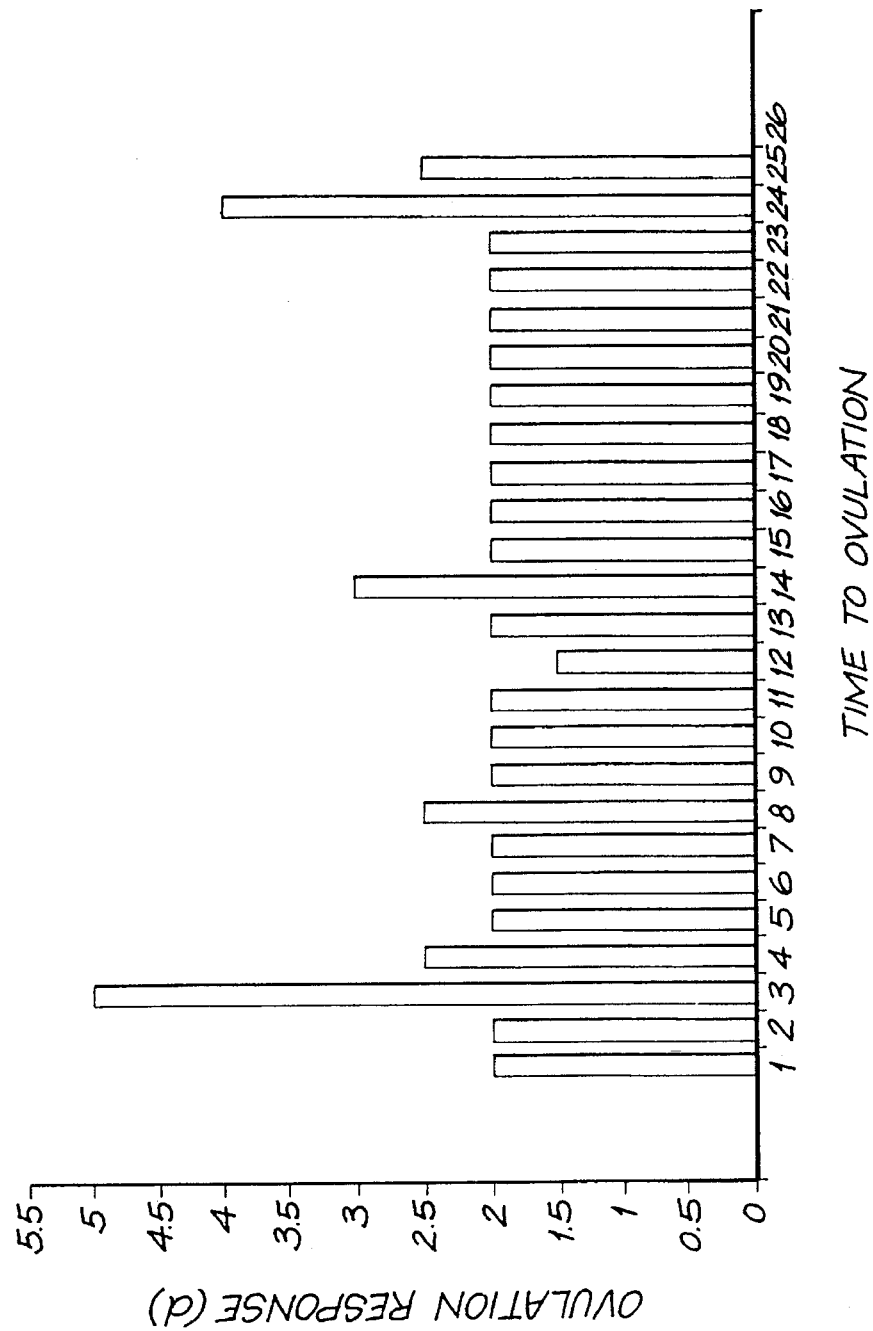

The procedure of Example 1 was repeated with twenty seven Hannovarian mares being given a short term implant containing 2.25 mg of Deslorelin. It can be assumed that those mares ovulating at 0–24 hours would have ovulated in the absence of treatment. The results obtained in this example are shown in FIG. 2.

EXAMPLE 3

Groups of mares were each given a placebo implant, a 1.3, 1.6 or 2.2 mg Deslorelin implant, or 5,000 iuhCG. The placebo treatment is designated 101 in FIG. 6 and the Deslorelin implants are indicated, respectively, as 102, 104 and 100.

It can be seen that the variation in ovulation was less for the 2.2 mg treatment than all other treatments; ovulation commonly occurred around 48 hours post-implantation with this treatment.

Some data has been removed from the analyses as outlyers in this trial. The criteria for removal was: those animals ovulating within 24 hours or 8+ days after implantation were considered not to have been affected by the implant. The numbers removed were 2×hCG; 5×100, 2 ×101, 0×102 and 2×104.

EXAMPLE 4

Mares with follicular size of at least 30 mm, as determined by ultrasound and rectal palpation, were allocated to one of three treatment groups. They were 2.2 mg Deslorelin implant, hCG (5000 iu) and untreated controls. It can be seen that ovulation commonly occurred around 2 days for the Deslorelin implanted and hCG injected mares. Untreated controls took significantly longer to ovulate from both implantation and from the start of oestrus than the treated groups. It appears that the untreated controls were in oestrus longer than treated animals.

TABLE 1

STUDY 1: Mean values of oestrus characteristics for three ovulation induction treatments.

| Characteristics | TREATMENTS | | |
|---|---|---|---|
| | LHRH | hCG | Control |
| No. day oestrus | 5.88 ± 1.27 | 5.46 ± 0.96 | 6.90 ± 2.42 |
| Day OV | 4.13 ± 0.35$^a$ | 4.40 ± 0.96$^a$ | 6.10 ± 1.79$^b$ |
| 30 mm to OV | 2.13 ± 0.35$^a$ | 2.00 ± 0.00$^a$ | 3.70 ± 1.49$^b$ |
| No. Ov's | 0.90 ± 0.56 | 1.10 ± 0.32 | 1.10 ± 0.32 |

EXAMPLE 5

Mares with follicular size of at least 30 mm, as determined by ultrasound and rectal palpation, at two locations (CSU and UCD) were allocated to one of five treatment groups. These treatment groups were a placebo implant, and implants containing 1.2 mg, 1.7 mg, 2.2 mg and 2.7 mg of Deslorelin. In this example the implant comprised finely ground calcium phosphate dihydrate, 8% by weight Lubritab and, where appropriate, the Deslorelin. A summary of the results obtained is provided in Table 2 which shows the mean time in hours to ovulation, standard deviation in hours of the time to ovulation, the number of mares in the sample and the percentage of mares ovulating within 48 hours.

TABLE 2

Summary statistics* for the time to ovulation by study location and Deslorelin does treatment group.

| | Treatment Group No. (Deslorelin dose. mg) | | | | |
|---|---|---|---|---|---|
| Center | 1 (0) | 2 (1.2) | 3 (1.7) | 4 (2.2) | 5 (2.7) |
| CSU - | | | | | |
| x | 68.00 | 49.00 | 48.00 | 46.91 | 44.00 |
| s | 38.74 | 8.02 | 11.44 | 3.62 | 9.34 |
| n | 12 | 12 | 12 | 11 | 12 |
| P | 50.0 | 75.0 | 83.3 | 100.0 | 100.0 |
| UCD - | | | | | |
| x | 91.50 | 66.00 | 58.50 | 46.50 | 58.29 |
| s | 35.68 | 37.40 | 45.10 | 10.01 | 32.81 |
| n | 8 | 8 | 8 | 8 | 7 |
| P | 25.0 | 75.0 | 87.50 | 87.50 | 85.71 |
| Combined - | | | | | |
| x | 77.40 | 55.80 | 52.20 | 46.74 | 49.26 |
| s | 38.44 | 25.01 | 29.21 | 6.81 | 21.50 |
| n | 20 | 20 | 20 | 19 | 19 |
| P | 40.0 | 75.0 | 85.0 | 94.7 | 94.74 |

*Summary statistics include the mean (x) and standard deviation (s) of the time to ovulation, the sample size (n), and the percent of mares ovulating within 48 hours (P).

The mares were mated and Table 3 summarises the pregnancy among the mares. This table provides the sample size, the number and percent of mares pregnant through a first cycle and the number and percent of mares pregnant through a second cycle.

TABLE 3

Summary* of pregnancy among study mares by study location and Deslorelin dose treatment group.

| | Treatment Group No. (Deslorelin dose. mg) | | | | |
|---|---|---|---|---|---|
| Center | 1 (0) | 2 (1.2) | 3 (1.7) | 4 (2.2) | 5 (2.7) |
| CSU | | | | | |
| n | 12 | 12 | 12 | 11 | 12 |
| $m_1$ | 5 | 8 | 8 | 8 | 8 |
| $P_1$ | 41.7 | 66.7 | 66.7 | 72.7 | 66.7 |
| $m_2$ | 7 | 11 | 11 | 10 | 9 |
| $P_2$ | 58.3 | 91.7 | 91.7 | 90.9 | 75.0 |
| UCD | | | | | |
| n | 8 | 8 | 8 | 8 | 7 |
| $m_1$ | 6 | 5 | 4 | 5 | 4 |
| $P_1$ | 75.0 | 62.5 | 50.0 | 62.5 | 57.1 |
| $m_2$ | 7 | 7 | **6 | **7 | **5 |
| $P_2$ | 87.5 | 87.5 | 75.0 | 87.5 | 71.4 |
| Combined | | | | | |
| n | 20 | 20 | 20 | 19 | 19 |
| $m_1$ | 11 | 13 | 12 | 13 | 12 |
| $P_1$ | 55.0 | 65.0 | 60.0 | 68.4 | 63.2 |
| $m_2$ | 14 | 18 | **17 | **17 | **14 |
| $P_2$ | 70.0 | 90.0 | 85.0 | 89.5 | 73.7 |

*Summary includes the sample size (n), the number ($m_1$) and percent ($P_1$) of mares pregnant through the first cycle, and the number ($m_2$) and percent ($P_2$) of mares pregnant through the second cycle.
**One mare in each of these study groups was not bred back.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

We claim:

1. A method for the controlled induction of ovulation in mares comprising implanting into a mare which already has an ovarian follicle approaching maturation a solid biocompatible implant comprising a solid carrier and an effective amount of an agonist of LHRH so as to increase the level of LHRH agonist in the mare above that prevailing immediately before that implantation.

2. A method as claimed in claim 1 in which the LHRH agonist is Deslorelin.

3. A method as claimed in claim 1 in which the LHRH agonist is present in the implant in an amount of from 1.0 to 5.0 mg.

4. A method as claimed in claim 3 in which the LHRH agonist is present in the implant in an amount of 1.5 to 3.0 mg.

5. A method as claimed in claim 4 in which the LHRH agonist is present in the implant in an amount of 2.0 to 2.4 mg.

6. A method as claimed in claim 1 in which the solid carrier comprises a biologically absorbable inorganic salt and an organic tablet-release compound.

7. A method as claimed in claim 1 in which the implant is embedded subcutaneously into the mare.

8. A method as claimed in claim 7 in which the implant is embedded into the mare through a tubular needle inserted into the mare, the implant being pushed down the needle with an obturator as the needle is withdrawn.

9. A solid biocompatible implant for controlling the induction of ovulation in mares which already have an ovarian follicle approaching maturation, the implant comprising a biologically absorbable solid and from 1.0 to 5.0 mg of an agonist of LHRH, wherein said implant is substantially cylindrical having a diameter of from 0.5 to 5.0 mm and a length of from 1.0 to 6.0 mm.

10. A biocompatible implant as claimed in claim 9 in which the LHRH agonist is Deslorelin.

11. A biocompatible implant as claimed in claim 9 in which the LHRH agohist is present in the implant in an amount of from 1.5 to 3.0 mg.

12. A biocompatible implant as claimed in claim 9 in which the LHRH agonist is present in the implant in an amount of from 2.0 to 2.4 mg.

13. A biocompatible implant as claimed in claim 9 in which the solid carrier comprises a biologically absorbable inorganic salt and an organic tablet release compound.

14. A biocompatible implant as claimed in claim 13 in which the inorganic salt is selected from the group consisting of calcium phosphate dihydrate, calcium phosphate, sodium sulphate and calcium carbonate.

15. A biocompatible implant as claimed in claim 13 in which the organic tablet release compound is selected from the group consisting of a fatty acid and a hydrogenated vegetable oil.

\* \* \* \* \*

UNITED STATES PATENT AND TRADEMARK OFFICE
CERTIFICATE OF CORRECTION

PATENT NO. : 5,545,408
DATED : August 13, 1996
INVENTOR(S) : Timothy E. Trigg, Edward L. Squires, Wolfgang Jochle It is certified that error appears in the above-indentified patent and that said Letters Patent is hereby corrected as shown below:

ON THE TITLE PAGE,
-- [75] Inventors: Timothy E. Trigg, Warrawee, Australia;
Edward L. Squires, Fort Collins, Colo.;
Wolfgang Jochle, Denville, N.J.--

Signed and Sealed this

Eighth Day of April, 1997

Attest:

BRUCE LEHMAN

*Attesting Officer*  *Commissioner of Patents and Trademarks*